US00PP26073P3

(12) United States Plant Patent
ten Have

(10) Patent No.: US PP26,073 P3
(45) Date of Patent: Nov. 10, 2015

(54) ***BEGONIA* HYBRID PLANT NAMED 'HVRIDARK'**

(50) Latin Name: *Begonia elatior*
Varietal Denomination: HVRIDARK

(71) Applicant: Jos ten Have, Maasland (DK)

(72) Inventor: Jos ten Have, Maasland (DK)

(73) Assignee: J and P Ten Have B.V. (NL)

( * ) Notice: Subject to any disclaimer, the term of this patent is extended or adjusted under 35 U.S.C. 154(b) by 166 days.

(21) Appl. No.: 13/998,300

(22) Filed: Oct. 18, 2013

(65) Prior Publication Data

US 2015/0113692 P1 Apr. 23, 2015

(51) Int. Cl.
*A01H 5/02* (2006.01)

(52) U.S. Cl.
USPC ..... Plt./344

(58) Field of Classification Search
USPC ..... Plt./343, 344
See application file for complete search history.

*Primary Examiner* — Anne Grunberg
(74) *Attorney, Agent, or Firm* — Cassandra Bright

(57) ABSTRACT

A new and distinct *Begonia elatior* cultivar named 'HVRIDARK' is disclosed, characterized by orange and yellow flowers, compact shape and green leaves. The new variety is a *Begonia elatior* typically produced as an ornamental plant.

1 Drawing Sheet

Latin name of the genus and species: *Begonia elatior.*
Variety denomination: 'HVRIDARK'.

BACKGROUND OF THE INVENTION

The new cultivar is the product of chance discovery. The new variety originated as a naturally occurring whole plant mutation of *Begonia elatior* 'HV01BI' U.S. Plant Pat. No. 22,643. *Begonia* 'HVRIDARK' is the same variety described in EU application number 2012/1922, grant pending.

The new variety was discovered by the inventor, Jos ten Have, a citizen of Netherlands, during 2011 in a commercial greenhouse belonging to the inventor in Maasland, Netherlands. After identifying the new variety as a potentially interesting selection, the inventor continued confidential testing and propagation of 'HVRIDARK', assessing stability of the unique characteristics of this variety.

Asexual reproduction of the new cultivar 'HVRIDARK' was first performed at a greenhouse in Maasland, Netherlands, by vegetative cuttings in Autumn of 2012. Access to all plants was restricted, as plants were kept in locations that are not open to the public. First sale of the new variety was during September of 2013. Through subsequent propagation multiple generations have been reproduced, which have shown that the unique features of this cultivar are stable and reproduced true to type.

SUMMARY OF THE INVENTION

The cultivar 'HVRIDARK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HVRIDARK.' These characteristics in combination distinguish 'HVRIDARK' as a new and distinct *Begonia elatior* cultivar:

1. Unique range and yellow colored flowers.
2. Compact plant shape.
3. Green leaves.
4. Full flowers with tepals and tepaloids, resulting in sterility as no reproductive organs are formed.
5. Good resistance to diseases and pests of *Begonia.*

PARENT COMPARISON

Plants of the new cultivar 'HVRIDARK' are similar to the parent, *Begonia elatior* 'HV01BI' in most horticultural characteristics. However the new variety, 'HVRIDARK' differs from 'HV01BI' in the following characteristics:

1. More compact in plant form than parent.
2. More intense flower coloration especially at margins.

COMMERCIAL COMPARISON

Plants of the new cultivar 'HVRIDARK' are best compared to the parent to the *Begonia elatior* 'HV01BI' U.S. Plant Pat. No. 22,643.

BRIEF DESCRIPTION OF THE PHOTOGRAPH

The accompanying photograph in FIG. 1 illustrates in full color a typical plant of 'HVRIDARK' grown in a commercial greenhouse in Maasland, Netherlands. This plant is approximately 8 to 10 weeks old, shown planted in a 0.8 liter pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'HVRIDARK' plants grown in a greenhouse in Maasland, Netherlands. This was done with a plant 8-10 weeks old in a 0.8 liter pot. Temperatures ranged from 18° C. at night to 20° C. during the day. No artificial light, photoperiodic treatments were given to the plants. No chemical treatments were given to plants. Measurements and numerical values represent averages of typical plant types.

Botanical classification: *Begonia elatior* 'HVRIDARK'.

PROPAGATION

Time to initiate roots: Summer: 30 to 35 days at approximately 22° C. Winter: 35 to 40 days at approximately 22° C.

Root description: Very thin, non-fleshy, non-fibrous, colored grey-brown; near RHS N199A.

Tuber description: No tubers present.

PLANT

Growth habit: Broad upright.

Height: 21.5 cm.

Plant spread: 27.2 cm.

Growth rate: Moderate.

Length of primary lateral branches: Average: 13.2 cm.

Quantity of primary lateral branches: Average: 5.

Characteristics of primary lateral branches:

- *Form.*—Rounded to elliptic.
- *Diameter.*—Average: 0.8 cm.
- *Color.*—Yellow-green; a in between RHS 146B and 148A, tinged near RHS 152B.
- *Texture.*—Moderately glossy, sparsely covered with short thin hairs, average length: 0.15 cm, coloured white, near RHS NN155D.
- *Strength.*—Moderately strong.

Internode length: Average: 3.1 cm.

FOLIAGE

Leaf:

- *Arrangement.*—Alternate.
- *Quantity.*—Approximately 5 per branch.
- *Average length.*—11.7 cm.
- *Average width.*—10.1 cm.
- *Shape of blade.*—Unequal ovate.
- *Apex.*—Acute.
- *Base.*—Hastate, touching to moderately overlapping.
- *Margin.*—Dentate, undulate.
- *Appearance of top surface.*—Glossy.
- *Appearance of bottom surface.*—Matte.
- *Pubescence.*—Upper side glabrous, under side very sparsely covered with short thin hairs, average length: 0.15 cm, colored white, near RHS NN155D.
- *Aspect.*—Undulating, with undulation stronger at margins.
- *Angle of attachment.*—Leaves attached at an average angle of 35° to lateral branch (=0°).
- *Color.*—Young foliage upper side: Green to yellow-green; in between RHS 143A and 144A but darker. Young foliage under side: Yellow-green; near RHS 148B. Mature foliage upper side: Green to yellow-green; in between RHS 139A and 147A but darker. Mature foliage under side: Yellow-green; near RHS 148B.
- *Venation.*—Type: Pinnate. Venation color upper side: Yellow-green; near RHS 144B. Venation color under side: Yellow-green; near RHS 144A and 144B.
- *Petiole.*—Length: Average: 5.5 cm. Diameter: Average: 0.5 cm. Color: Yellow-green; near RHS 152B. Texture: Glossy, very sparsely covered with short thin hairs, average length: 0.15 cm, colored white, near RHS NN155D.
- *Stipule description.*—Length: Average: 1.1 cm. Diameter: Average: 1.0 cm. Color: Yellow-green; near RHS 145B. Texture: Glabrous, moderately glossy.

FLOWER

Natural flowering season: Typically Spring and Summer blooming plant.

Days to flowering from rooted cutting: 8 weeks.

Inflorescence and flower type and habit: Compound cyme.

Rate of flower opening: 7 to 10 days from bud to fully opened flower.

Flower longevity on plant: Average: 10 days.

Persistent or self-cleaning: Self-cleaning.

Bud:

- *Shape.*—Flabellate.
- *Length.*—Average: 1.3 cm.
- *Diameter.*—Average: 1.5 cm.
- *Color.*—Yellow-green; near RHS 144D, top edge red; near RHS 41B and 41C.

Flower size:

- *Diameter.*—Average: 5.5 cm.
- *Depth.*—Average: 2.4 cm.

Tepals: In *Begonia* no separate petals and sepals are present, only tepals, as described here:

- *Quantity.*—Average: 2.
- *Arrangement.*—Opposite.
- *Length.*—Average: 3.7 cm.
- *Width.*—Average: 4.4 cm.
- *Shape.*—Reniform.
- *Apex.*—Rounded.
- *Base.*—Reniform.
- *Margin.*—Entire, slightly undulate.
- *Texture, upper and lower surfaces.*—Upper surface glabrous, matte, moderately velvety, lower surface glabrous, moderately glossy.
- *Color.*—When opening, upper surface: Green-yellow; near RHS 1C, margins red; near RHS 43A and 43B. When opening, lower surface: Yellow-green; near RHS 150C and 154C, margins red; near RHS 43A. Fully opened, upper surface: Orange; near RHS 26B, base yellow-green; near RHS 150C, margins red; RHS 43A and 45C. Fully opened, lower surface: Yellow-green; near RHS 150C and 154C, margins red; near RHS 43A and 43B.

Sepals: In *Begonia* no separate petals and sepals are present, only tepals, as described above (under "Tepals"):

Tepaloids:

- *Quantity.*—Average: 24.
- *Arrangement.*—Rotate.
- *Length.*—Average: 1.8 cm (varying from 0.8 cm to 2.3 cm).
- *Width.*—Average: 1.9 cm (varying from 0.9 cm to 3.0 cm).
- *Shape.*—Broad obovate to near orbicular.
- *Apex.*—Rounded.
- *Base.*—Cuneate.

*Margin.*—Irregular denticulate.

*Texture, upper and lower surfaces.*—Upper surface glabrous, matte, moderately velvety, lower surface glabrous, moderately glossy.

*Color.*—When opening, upper surface: Green-yellow; near RHS 1B and 1C, margins orange-red; near RHS 32A and 32B. When opening, lower surface: Green-yellow; near RHS 1C, margins red; near RHS 42C and 42D. Fully opened, upper surface: Yellow; near RHS 6C and 6d, margins Red; near RHS 41A. Fully opened, lower surface: Yellow-green; near RHS 154C, margins red; near RHS 43A and 43B.

Peduncles:

*Length.*—Average: 4.6 cm.

*Diameter.*—Average: 0.5 cm.

*Angle.*—About 30° to the lateral branch.

*Strength.*—Moderate.

*Texture.*—Glabrous, moderately glossy.

*Color.*—Yellow-green; near RHS 145A and 145B.

REPRODUCTIVE ORGANS

No reproductive organs present.

OTHER CHARACTERISTICS

Seeds and fruits: No seeds/fruits are formed.

Disease/pest resistance: Higher than usual resistance to the normal diseases and pests of similar *Begonia* varieties.

Temperature tolerance: USDA zone 10 to 12.

What is claimed is:

1. A new and distinct cultivar of *Begonia elatior* plant named 'HVRIDARK' as herein illustrated and described.

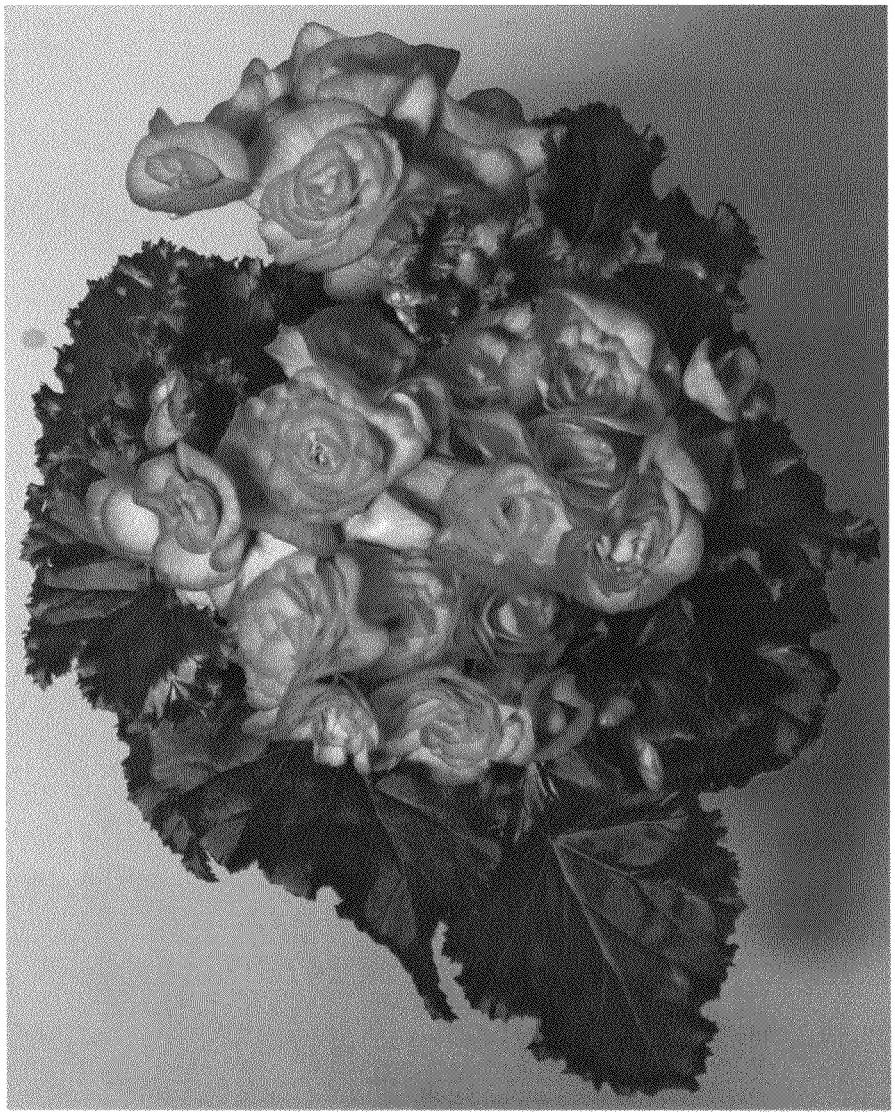

* * * * *